United States Patent [19]

Andreiko

[11] Patent Number: 5,238,404
[45] Date of Patent: Aug. 24, 1993

[54] ORTHODONTIC BRACE FOR POSITIONING TEETH

[75] Inventor: Craig A. Andreiko, Alta Loma, Calif.
[73] Assignee: Ormco Corporation, Glendora, Calif.
[21] Appl. No.: 875,251
[22] Filed: Apr. 27, 1992
[51] Int. Cl.$^5$ .............................................. A61C 3/00
[52] U.S. Cl. ......................................................... 433/20
[58] Field of Search .............................. 433/8, 9, 16, 20

[56] References Cited

U.S. PATENT DOCUMENTS

| | | | |
|---|---|---|---|
| 1,014,028 | 1/1912 | Angle | 433/20 |
| 2,379,011 | 6/1945 | Laskin | 433/16 |
| 3,043,007 | 7/1962 | Wallshein | 433/20 |
| 3,660,900 | 5/1972 | Andrews | 433/16 |
| 3,686,757 | 8/1972 | McVickers et al. | 433/5 |
| 3,772,789 | 11/1973 | De Woskin | 433/5 |
| 3,921,295 | 11/1975 | James | 433/21 |
| 4,363,624 | 12/1982 | Johnston | 433/9 |
| 4,479,779 | 10/1984 | Wool | 433/20 |
| 4,551,094 | 11/1985 | Kesling | 433/8 |

Primary Examiner—John J. Wilson
Attorney, Agent, or Firm—Wood, Herron & Evans

[57] ABSTRACT

Apparatus is provided for resetting the position of teeth in a patient's mouth to a desired configuration where each tooth requires an individual magnitude of force, dependent upon the positioning of such tooth in the patient's mouth, to reset such tooth to the desired configuration. The apparatus includes a plurality of bracket assemblies each including a support member and a pad. Each pad is adhered to an individual one of the patient's teeth and to the associated support member. A groove is provided in each of the support members. An arch wire extends through the groove in each of the support members for retention in the groove. The arch wire has at each groove a thickness (or cross-sectional area) dependent upon the individual magnitude of force to be applied to the associated tooth. The thickness (or cross-sectional area) of the arch wire may vary progressively between adjacent bracket assemblies in accordance with the differences in the thicknesses (or cross-sectional area) of the arch wire at the positions of the grooves in such adjacent bracket assemblies. Alternatively, the thickness (or cross-sectional area) of the arch wire at the position of the groove in each bracket assembly may vary substantially only at the position of such groove from the thickness of the arch wire at the adjacent grooves.

8 Claims, 2 Drawing Sheets

ORTHODONTIC BRACE FOR POSITIONING TEETH

This invention relates to orthodontic braces. More particularly, the invention relates to orthodontic braces which apply, to each tooth in a patient's mouth, an individual magnitude of force related to the magnitude of force required to reset the position of such tooth to a desired configuration in the patient's mouth.

When the teeth in a patient's mouth are displaced from an even or uniform disposition, such displacements tend to produce problems over an extended period of time. For example, such displacements may produce problems in the patient's gums. These problems may cause the retention of teeth by the patient's gums to be weakened so that the teeth so that the teeth become loose in the patient's mouth. The problem may become so aggravated that the teeth may eventually have to be removed from the patient's mouth.

To prevent the conditions in a patient's mouth from deteriorating, orthodontists often attempt to reset the positions of the teeth in the patient's mouth. The orthodontists do this by attaching braces to the patient's teeth and by gradually adjusting the forces applied by the braces to the teeth. These forces act against the teeth in the patient's mouth to move the teeth gradually toward the positions desired by the orthodontist.

The braces are generally formed by bracket assemblies (each defined by a support member and a pad) and an arch wire supported in a groove in each of the support members. The pad in each bracket assembly may be in the form of a mesh which is adhered to an individual tooth and the support member is attached to the pad. The arch wire extends between the support members in the bracket assemblies on adjacent teeth and applies a force to the teeth to move the teeth toward their desired positions. As the arch wire moves the teeth toward the positions predetermined by the patient's orthodontist, the orthodontist can adjust the brace to vary the forces imposed by the arch wire on the teeth.

Each tooth in a patient's mouth requires an individual magnitude of force to be applied to the tooth to reset the position of the tooth to a desired configuration relative to the other teeth in the patient's mouth. For example, the force required to move a molar tooth in the patient's mouth is greater than the force required to move a bicuspid tooth in a patient's mouth. Similarly, the force required to move a front tooth in a patient's mouth is greater than the magnitude of the force required to move a bicuspid tooth in a patient's mouth but less than the magnitude of the force required to move a molar tooth in the patient's mouth.

Attempts have been made to provide a controlled magnitude of force on each tooth in a patient's mouth. For example, in U.S. Pat. No. 3,772,789 issued to Irvin S. De Weoskin on Nov. 20, 1973, for an "Orthodontic Tensioning Assembly", a progressively increased magnitude of force is applied by a brace against the abutting teeth at progressive positions along the brace. In U.S. Pat. No. 3,686,757 issued to Jack C. McVickers et al on Aug. 29, 1972, for a "Constant Tension Orthodontic Appliance" and in U.S. Pat. No. 3,921,295 issued to John Oliver James on Nov. 25, 1975, for an "Orthodontic Device", a substantially constant force is applied to a patient's teeth at progressive positions along a brace.

In spite of efforts to regulate the magnitude of the force applied by a brace to different teeth in a patient's mouth as evidenced by the patents specified in the previous paragraph, no one has apparently regulated such force in a practical manner. Specifically, no one has regulated the magnitude of the force applied to each individual tooth in the patient's mouth in accordance with the magnitude of the force required to move such tooth to a desired position in the patient's mouth. The problem still exists even though it has been known to exist for some time and even though substantial amounts of money have been expended, and a significant effort has been made, to solve such problem.

This invention provides apparatus which solves the problems discussed in the previous paragraph. The apparatus constituting this invention provides a brace which imposes an individual magnitude of force against each tooth in a patient's mouth. This magnitude of force for each tooth is dependent upon the magnitude of the force required to reset the position of such tooth in the patient's mouth. For example, the greatest magnitude of force is applied by the brace against the molars in a patient's mouth; a decreased force is applied against the front teeth in the patient's mouth; and an even lesser force is applied against the bicuspids in the patient's mouth. In this way, the magnitude of the force applied against each tooth by the brace is only that sufficient to reset the position of such tooth to the desired configuration relative to the other teeth in the patient's mouth.

In one embodiment of the invention, apparatus is provided for resetting the position of teeth in a patient's mouth to a desired configuration where each tooth requires an individual magnitude of force, dependent upon the positioning of such tooth in the patient's mouth, to reset such tooth to the desired configuration. The apparatus includes a plurality of bracket assemblies each including a support member and a pad. Each pad is adhered to an individual one of the patient's teeth and to the associated support member. A groove is provided in each of the support members. An arch wire extends through the groove in each of the support members for retention in the groove.

The arch wire has at each groove a thickness (or cross-sectional area) dependent upon the individual magnitude of force to be applied to the associated tooth. The thickness (or cross-sectional area) of the arch wire may vary progressively between adjacent bracket assemblies in accordance with the differences in the thicknesses (or cross-sectional area) of the arch wire at the positions of the grooves in such adjacent bracket assemblies. Alternatively, the thickness (or cross-sectional area) of the arch wire at the position of the groove in each bracket assembly may vary substantially only at the position of such groove from the thickness of the arch wire at the adjacent grooves.

Figure 4:
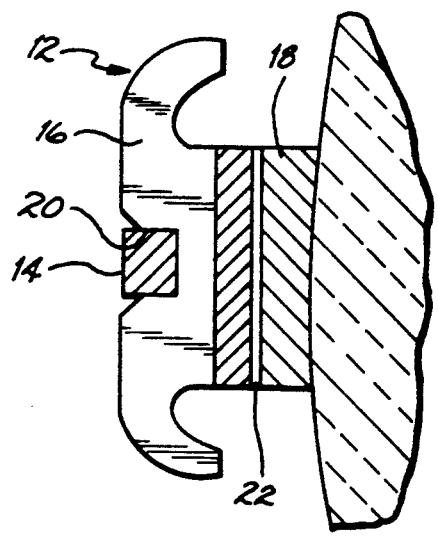
FIG. 4 is an enlarged sectional view of the bracket assembly shown in FIG. 3 and is taken substantially on the line 4—4 of FIG. 2.

In one embodiment of the invention, a brace generally indicated at 10 is provided. The brace 10 includes a plurality of bracket assemblies generally indicated at 12 and an arch wire 14. Each bracket assembly 12 includes a support member 16 and a pad 18. The pad 18 may be made from a mesh and may be adhered at one surface to a patient's tooth. At its other surface, the pad 18 may be adhered as by an alloy 22 (FIG. 4) to the associated support member 16. The support member 16 and the pad 18 are adapted to be made from a suitable material such as stainless steel so as to be impervious to the acids in a patient's body. The support member 16 and the pad 18 may be provided with a conventional construction.

The support member 16 may be provided with a groove 20 which is shaped to receive the arch wire 14. By attaching a different bracket assembly 12 to each individual tooth and by controlling the depth, angle and position of the groove 20 in each support member 16, the arch wire 14 disposed in the groove can be provided with a force to reset the position of the teeth in a patient's mouth.

Figure 1:
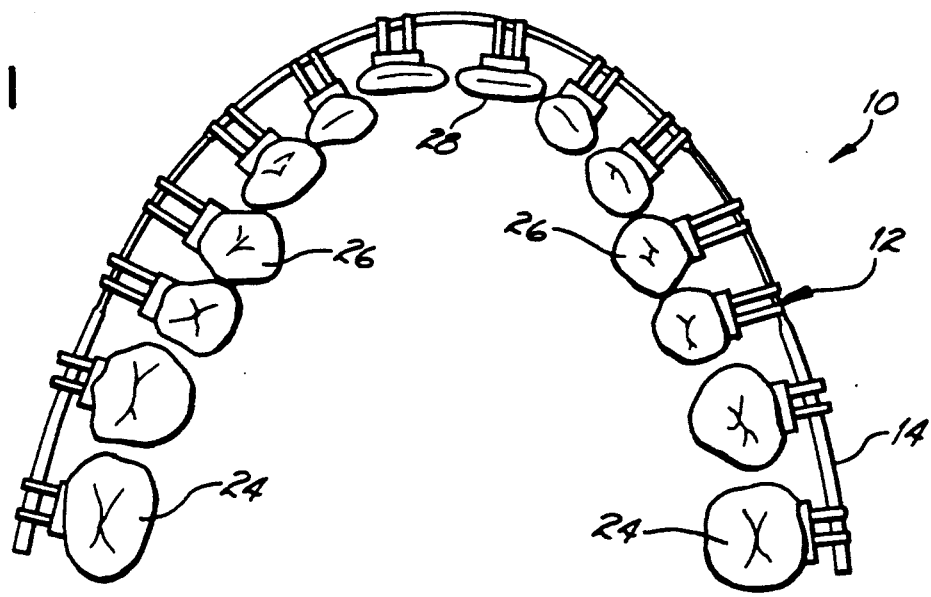
FIG. 1 is a plan view schematically of a set of teeth in a patient's mouth and a brace supported by the teeth to adjust the positioning of the teeth, the brace including a plurality of brackets and an arch wire.
Figure 2:
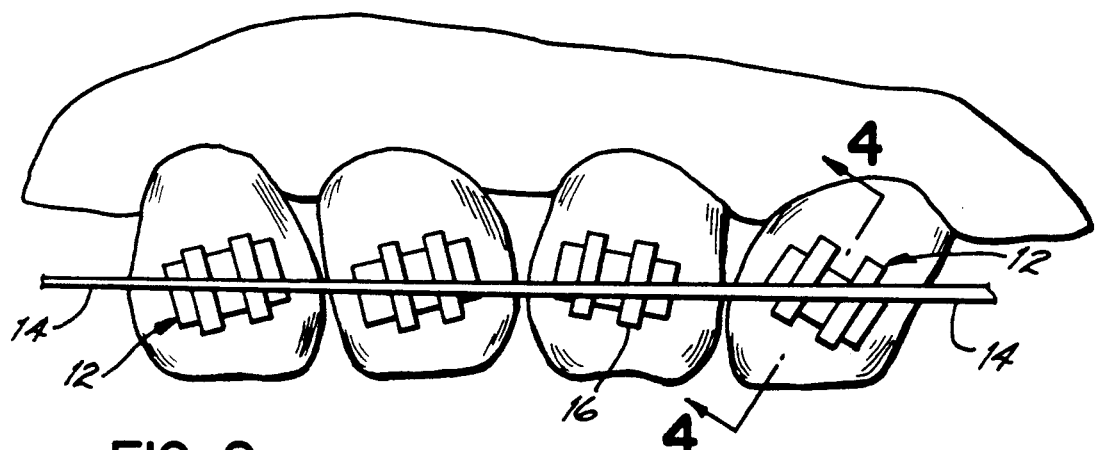
FIG. 2 is an enlarged schematic front elevational view of a plurality of teeth in a patient's mouth and of a brace formed from a plurality of the bracket assemblies and the arch wire and applied to the teeth to reset the position of the teeth to a desired configuration in the patient's mouth.
Figure 3:
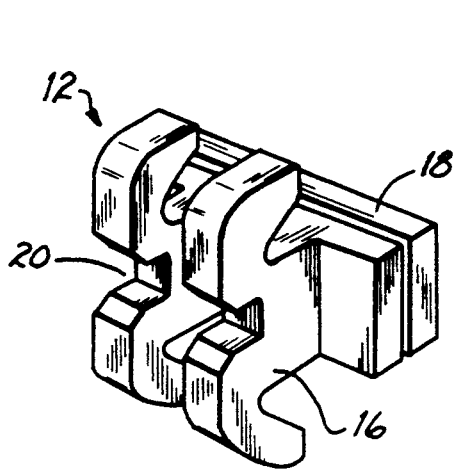
FIG. 3 is an enlarged perspective view illustrating the construction of one of the bracket assemblies shown in FIGS. 1 and 2.
Figure 7:
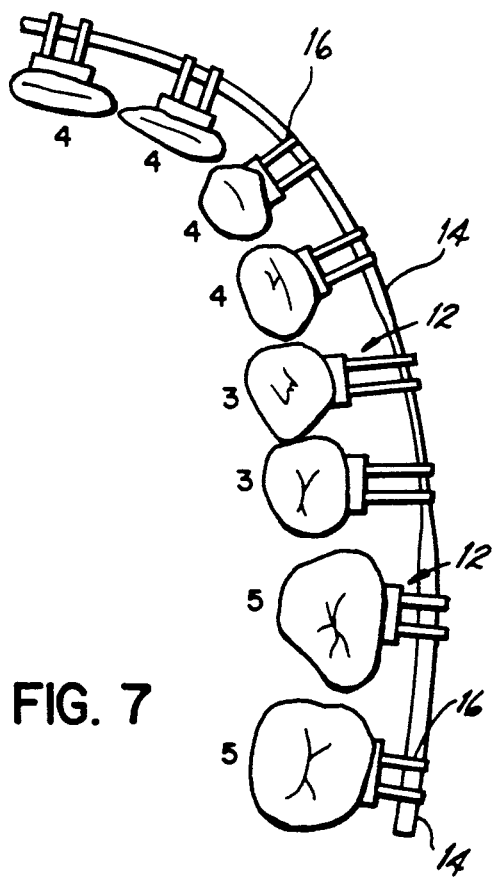
FIG. 7 is a front elevational view of several teeth, including molars, bicuspids and front teeth, in a patient's mouth and schematically illustrates the magnitudes of the forces which have to be applied to the individual teeth to reset the position of the teeth to the desired configuration in the patient's mouth.

There are different types of teeth in a patient's mouth. Molar teeth 24 (FIG. 1) are disposed at the rear of the patient's mouth and are constructed and set in the mouth so that forces of large magnitude are required to move the teeth. This is indicated schematically in FIG. 7 by the numeral "5", which indicates the relative root strength of the molars in the patient's mouth. Bicuspid teeth 26 (FIG. 1) are disposed adjacent the molars in the patient's mouth. The root strength of the bicuspids is relatively low in comparison to the molars, as indicated schematically by the numeral "3" in the bicuspids in FIG. 7. Front teeth 28 (FIG. 1) are further removed in the patient's mouth from the molars than are the bicuspids. The root strength of the front teeth is between the root strengths of the molars and the bicuspids. This is indicated schematically by the numeral "4" in FIG. 7. It will be indicated that the numerals "3", "4" and "5" are relative numbers only for purposes of illustration and are not absolute numbers.

It would be desirable to impose upon each tooth in a patient's mouth only the force required to reset the position of the tooth to a desired configuration relative to the other teeth in the patient's mouth. Until now, now one has been able to provide this. This invention accomplishes this in a relatively simple and straight forward manner when seen in retrospect.

In this invention, the arch wire 14 is provided with different thickness (or cross-sectional areas) at different positions along the length of the arch wire. The thickness (or cross-sectional area) of the arch wire 14 at the position of each individual tooth is dependent upon the force to be applied by the arch wire to that tooth. For example, a maximum force may be applied by the arch wire 14 against the molars 24; an intermediate force may be applied by the arch wire 14 against the front teeth 28; and a reduced force may be applied by the arch wire 14 against the bicuspids 26.

Figure 5:
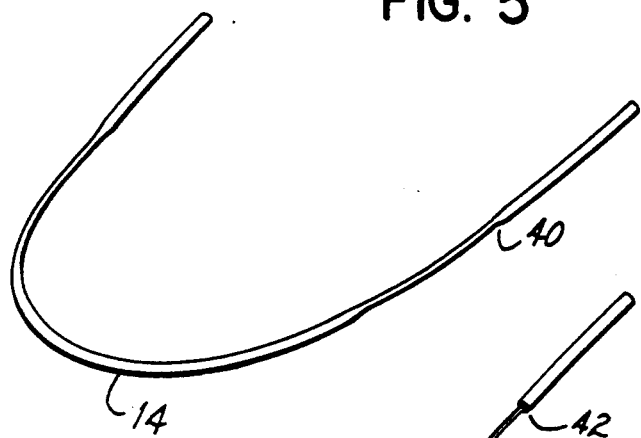
FIG. 5 is a schematic perspective view of one embodiment of an arch wire included in the brace shown in FIG. 1 and illustrates the thickness of the arch wire at progressive positions along the arch wire.
Figure 6:
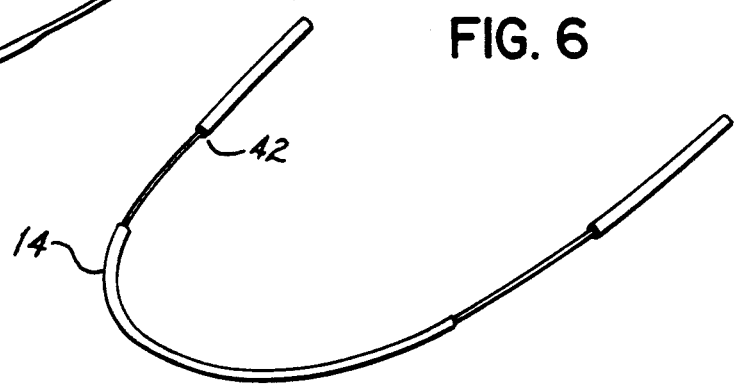
FIG. 6 is a schematic perspective view of another embodiment of an arch wire capable of being included in the brace shown in FIG. 1 and illustrates the thickness of the arch wire at progressive positions along the arch wire.

FIGS. 5 and 6 illustrate two (2) different embodiments of the arch wire 14 for providing at each individual tooth a thickness (or cross-sectional area) dependent upon the force required to reset the position of such tooth to a desired configuration relative to that of the other teeth in the patient's mouth. In the embodiment shown in FIG. 5, the thickness (or cross-sectional area) varies progressively (as at 40) in the portion of the arch wire 14 between the groove 20 in each bracket assembly. In the embodiment shown in FIG. 6, the thickness (or cross-sectional area) of the arch wire 14 remains substantially constant in the distance between adjacent grooves 20. In the embodiment shown in FIG. 6, the thickness (or cross-sectional area) of the arch wire 14 varies relatively quickly (as at 42) at the positions near the grooves and remains substantially constant throughout the length of the grooves. It will be appreciated that the thickness of the arch wire 14 may be different from the configuration of FIGS. 5 and 6 without departing from the scope of the invention. For example, the thickness of the arch wire 14 may vary progressively and then abruptly, all in the distance between adjacent teeth, to adjust the thickness of the arch wire to the thickness desired for the arch wire for such adjacent teeth.

Figure 8:
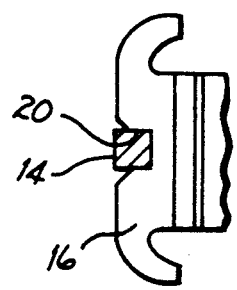
FIG. 8 is an enlarged side elevational view, partially in section, of a bracket assembly and illustrates a particular disposition of the arch wire in the groove in this bracket assembly.
Figure 9:
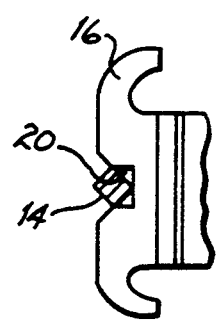
FIG. 9 is an enlarged side elevational view, partially in section, of a bracket assembly and illustrates another possible disposition of the arch wire in the groove in this bracket assembly.
Figure 10:
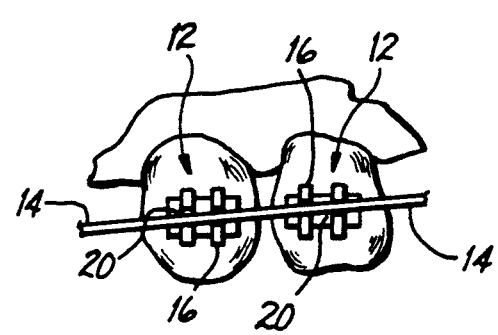
FIG. 10 is an enlarged front elevational view of a pair of successive bracket assemblies and illustrates a further possible disposition of the arch wire in the grooves in such bracket assemblies.

FIGS. 8, 9 and 10 schematically illustrate different ways in which the arch wire 14 may be disposed in the grooves 20. It will be appreciated that the schematic illustrations shown in FIGS. 8, 9 and 10 are only exemplary and that other dispositions of the arch wire 14 in the grooves 20 may occur. FIG. 8 shows the arch wire 14 snugly disposed in the groove 20 with the sides of the arch wire in flush relationship with the walls of the groove.

In FIG. 9, the arch wire 14 is twisted relative to the walls of the groove 20 so that only the corners of the arch wire engage the walls of the groove. This relationship may be provided when the height of the groove 20 is larger than the thickness of the arch wire. In this relationship, the arch wire 14 is able to twist in a counterclockwise direction relative to the walls of the groove but is unable to twist relative to the walls of the groove in a clockwise direction.

FIG. 10 is a front elevational view illustrating a pair of successive teeth in a patient's mouth and further illustrating bracket assemblies 12 associated with such teeth. In FIG. 10, the grooves 20 in such bracket assemblies 12 are at different heights. Under such circumstances, the arch wire 14 extends linearly upwardly from the left bracket assembly to the right bracket assembly and engages the walls of the left groove 20 at the lower left end of such groove and the walls of the right groove 20 at the upper right end of such groove so that the arch wire is retained in a fixed position in each in the grooves.

Because of the difference in the thickness of the arch wire 14 at each of the grooves, the manner of disposing the arch wire 14 in the grooves may take different forms such as those discussed in the previous paragraph. It is believed that the particular disposition of the arch wire 14 in each groove 20 as a result of the individual thickness of the arch wire at the position of each groove will be within the knowledge of a person of ordinary skill in the art.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination for resetting the position of teeth in a patient's mouth to a desired configuration,
   a plurality of bracket assemblies each having a groove and each constructed to be applied to an individual one of the patient's teeth to apply a force to such individual tooth for resetting the position of such tooth to the desired configuration, and
   an arch wire extending through the groove in each bracket assembly to apply a force to such bracket assembly to reset the position of the tooth associated with such bracket assembly,
   the arch wire being constructed to apply to each bracket assembly a force related to the force required to reset the position of the associated tooth, the arch wire having an extended length and being provided, at the position of the groove in each bracket assembly, with an individual thickness related to the force required to reset the position of the associated tooth to the desired configuration, the thickness of the arch wire varying progressively between adjacent bracket assemblies in accordance with the individual thickness of the arch wire at the positions of the grooves in such adjacent bracket assemblies.

2. In combination for resetting the position of teeth in a patient's mouth to a desired configuration,
   a plurality of bracket assemblies each having a groove and each constructed to be applied to an individual one of the patient's teeth to apply force to such individual tooth for resetting the position of such tooth to the desired configuration, and
   an arch wire extending through the groove in each bracket assembly to apply a force to such bracket assembly to reset the position of the tooth associated with such bracket assembly,
   the arch wire being constructed to apply to each bracket assembly a force related to the force required to reset the position of the associated tooth, the arch wire having an extended length and being provided, at the position of the groove in each bracket assembly, with an individual thickness related to the force required to reset the position of the associated tooth to the desired configuration, the thickness of the arch wire at the position of the groove in each bracket assembly varying abruptly to obtain at such groove the individual thickness related to the force required to reset the position of the associated tooth to the desired configuration.

3. In a combination as set forth in claim 2, the thickness of the arch wire also varying progressively between at least one adjacent pair of bracket assemblies in accordance with the individual thickness of the arch wire at the position of the groove in each bracket.

4. In combination for resetting the position of teeth in a patient's mouth to a desired configuration where each of the teeth requires an individual amount of force, dependent upon the positioning of such tooth in the patient's mouth, to reset such tooth to the desired configuration,
   a plurality of bracket assemblies each including a support member and a pad, each pad being constructed to be adhered to an individual one of the patient's teeth and to the associated support member,
   a groove in each of the support members, and
   an arch wire having an extended length and extending through the groove in each of the support members for retention in the slot and having a construction at each of the slots to apply the individual amount of force to the associated tooth,
   each of the grooves and the arch wire at the position of such grooves being constructed and disposed relative to each other to provide for a retention of the arch wire in the groove,
   the arch wire being provided at each groove with a thickness dependent upon the individual amount of force to be applied to the associated tooth, the thickness of the arch wire varying progressively between adjacent bracket assemblies in accordance with the individual thickness of the arch wire at the positions of the grooves in such adjacent bracket assemblies.

5. In a combination as set forth in claim 4,
   at least some of the grooves being defined by walls disposed substantially parallel to the associated tooth and the arch wire being retained tightly in such grooves and in substantially flush relationship with the walls of such grooves.

6. In a combination as set forth in claim 4,
   at least some of the grooves being defined by walls disposed substantially parallel to the associated tooth and the arch wire being twisted relative to the walls of such grooves to be retained within such grooves.

7. In a combination as set forth in claim 4,
   at least some of the adjacent grooves being defined by walls disposed substantially parallel to the associated teeth and the arch wire extending in a linear direction through the grooves at an angle to the grooves for retention by the opposite corners of the walls defining the grooves in adjacent teeth.

8. In combination for resetting the position of teeth in a patient's mouth to a desired configuration where each of the teeth requires an individual amount of force, dependent upon the positioning of such tooth in the patient's mouth, to reset such tooth to the desired configuration,
   a plurality of bracket assemblies each including a support member and a pad, each pad being constructed to be adhered to an individual one of the patient's teeth and to the associated support member, a groove in each of the support members, and an arch wire having an extended length and extending through the groove in each of the support members for retention in the slot and having a construction at each of the slots to apply the individual amount of force to the associated tooth, each of the grooves and the arch wire at the position of such grooves being constructed and disposed relative to each other to provide for a retention of the arch wire in the groove, the arch wire being provided at each groove with a thickness dependent upon the individual amount of force to be applied to the associated tooth, the thickness of the arch wire at the position of the groove in each bracket assembly varying abruptly to obtain at such groove the individual thickness related to the force required to reset the position of the associated tooth to the desired position.

* * * * *